United States Patent [19]

Fugo

[11] Patent Number: 5,413,574
[45] Date of Patent: May 9, 1995

[54] METHOD OF RADIOSURGERY OF THE EYE

[76] Inventor: Richard J. Fugo, 1507 Plymouth Blvd., Norristown, Pa. 19401

[21] Appl. No.: 134,805

[22] Filed: Oct. 8, 1993

Related U.S. Application Data

[63] Continuation-in-part of Ser. No. 940,448, Sep. 4, 1992.

[51] Int. Cl.$^6$ .............................................. A61B 17/36
[52] U.S. Cl. ........................................ 606/33; 606/34; 606/39; 128/898
[58] Field of Search ................................. 606/32-35, 606/37-42, 45-50

[56] References Cited

U.S. PATENT DOCUMENTS

| | | |
|---|---|---|
| 3,884,237 | 5/1975 | O'Malley et al. . |
| 3,913,583 | 10/1975 | Bross . |
| 4,301,802 | 11/1981 | Poler . |
| 4,326,529 | 4/1982 | Doss et al. . |
| 4,494,539 | 1/1985 | Zenitani et al. ........................ 606/33 |
| 4,534,347 | 8/1985 | Taylor ................................. 606/33 |
| 4,597,388 | 7/1986 | Koziol et al. . |
| 4,805,616 | 2/1989 | Pao . |
| 5,009,656 | 4/1991 | Reimels . |
| 5,217,459 | 6/1993 | Kamerling . |

OTHER PUBLICATIONS

Krause-Hohenstein, "Electrosurgery: . . . " Quintessence Intnl, Report 2252, 1983.

Ellman Catalog, "What's New in Office Ophthalmology".

Clark, Douglas and Asnis, "Electrothermic Methods in the Treatment of Neoplasma and Other Lesions," Radiology, vol. 2, 233-246 (1924).

Ward, "Value of Electrothermic Methods in the Treatment of Malignancy," J.A.M.A., vol. 84, 660-6666 (1925).

Wyeth, "Surgery of Neoplastic Diseases by Electrothermic Methods," Paul B. Hoeber, Inc., 3-6 (1926).

McLean, "The Bovie Electrosurgical Generator," Archives of Surgery, vol. 18, 1863-1873 (1929).

Ellis, "The Rate of Healing of Electrosurgical Wounds as Expressed by Tensile Strength," J.A.M.A., vol. 96, 16-18 (1931).

Burgess, "Electrosuryery," Lancet, vol. 2, 1355-1359 (1993).

Schwan, Carstensen and Li, "Heating of Fat-Muscle Layers by Electromagnetic and Ultrasonic Diathermy," Transactions and Bimonthly Publications AIEE, 6:483 (9), 483-487 (1953).

Aronow, "The Use of Radio-frequency Power in Making Lesions in the Brain," Journal of Arch. Phys. Med., vol. 17, 431-438 (1960).

Peyman and Dodich, "Experimental Intraocular Coagulation," Ophthalmic Surgery, vol. 3, No. 1, 32-37 (1972).

Friedman, "The Technical Aspects of Electrosurgery," Oral Surgery, Oral Medicine and Oral Pathology, vol. 36, 177-187 (1973).

Curtis, "High Frequency Currents in Endoscopy: A review of Principles and Precautions," Gastrointestinal Endoscopy, vol. 20, No. 1, 9-12 (1973).

(List continued on next page.)

*Primary Examiner*—Stephen C. Pellegrino
*Assistant Examiner*—Michael Peffley
*Attorney, Agent, or Firm*—Michael F. Petock

[57] ABSTRACT

A method of ocular surgery wherein low power radio waves are transmitted from the tip of an active incising electrode and used to make incisions in the tissues of the eye. A high impedance contact is provided between the surgical subject and a grounding plate connected to the radio wave generator. The use of the low power radio wave energy and the high impedance contact prevents the active incising electrode from becoming hot and causing damage to sensitive tissues of the eye.

21 Claims, No Drawings

OTHER PUBLICATIONS

Sozio, Riley and Shklar, "Histologic and Electronic Evaluation of Electrosurgical Currents: Nonfiltered Full-wave Modulated vs. Filtered Current," Journal of Prosthetic Dentistry, vol. 33, No. 3, 300–311 (1975).

Maness, Roeber, Clark, Cataldo, Riis and Haddad, "Histologic Evaluation of Electrosurgery with Varying Waveforms," Journal of Prosthetic Dentistry, vol. 40, No. 3, 304–308 (1978).

Krause-Hohenstein, "Electrosurgery: Fundamental Requirements for Successful Use (I)," Quintessence International, Report 2252, Nov. 1115–1124 (1983).

Ellman, "What's New in Office Ophthalmology?".

Heilmann and Paton, "Atlas Ophthalmic Surgery," vol. II (1987) pp. 2.2–2.16.

Krupin, "Manual of Glaucoma—Diagnosis and Management," (1988) pp. 204–216.

"Glaucoma," Official Journal of the International Glaucoma Congress, vol. 9, No. 4, Jul./Aug. (1987) pp. 128–133.

L'Esperance, "Ophthalmic Lasers—Photocoagulation, Photoradiation, and Surgery," Second Edition (1983) pp. 505–512.

"Force Instruction Manual," of Valleylab, Inc. (1991).

METHOD OF RADIOSURGERY OF THE EYE

CROSS REFERENCE TO RELATED APPLICATION

This application is a continuation-in-part application of application Ser. No. 07/940,448 filed Sep. 4, 1992, by the inventor herein and entitled RADIOSURGERY OF THE EYE.

FIELD OF THE INVENTION

This invention relates to ocular surgical procedures, specifically to ocular surgical procedures employing the use of low power radio waves to effect incision of ocular tissue.

BACKGROUND OF THE INVENTION AND DESCRIPTION OF PRIOR ART d'Arsonval, in 1890, studied the effects of electric currents on biologic tissue. High frequency electromagnetic energy has been employed in numerous surgical procedures and is primarily used to perform the functions of cutting, coagulation, and dessication.

Clark, Douglas and Asnis in "Electrothermic Methods in the Treatment of Neoplasms and Other Lesions, with Clinical and Histological Observations," Radiology, Vol. 2, 233–246 (1924), emphasized the importance of electrothermic dessication and coagulation in the removal of various tumors and lesions in the body. Ward in "Value of Electrothermic Methods in the Treatment of Malignancy," J.A.M.A., Vol. 84, 660–666 (1925), discussed the use of the endotherm knife, which used high frequency electromagnetic energy to make surgical incisions, and distinguished the processes of cautery and electrocoagulation and electrodessication, the former process applying heat to tissues by means of a hot object, and the latter two processes creating heat in tissues by means of the resistance of the tissues to the passage of an electrical current. Wyeth in his text, "Surgery of Neoplastic Diseases by Electrothermic Methods," Paul B. Hoeber, Inc. (1926), detailed the use of high frequency electrical currents in various neoplastic surgeries and classified the method as endothermy, which classification encompassed dessication, coagulation and cutting functions carried out by means of monopolar and bipolar currents and the endotherm knife.

McLean, in his article "The Bovie Electrosurgical Generator," Archives of Surgery, Vol. 18, 1863–1873 (1929), explained the cutting and deep heating effects of damped and undamped waveforms, noting that cutting functions required a higher current density than was needed for deep heating effects. In his article "The Rate of Healing of Electrosurgical Wounds as Expressed by Tensile Strength," J.A.M.A., Vol. 96, 16–18 (1931), Ellis compared the healing rates of electrically induced incisions with those of incisions made with a scalpel. Burgess, in "Electrosurgery," Lancet, Vol. 2, 1355–59 (1933), discussed techniques of using an electrode to cut body tissues. Schwan, Carstensen, and Li, in "Heating of Fat-Muscle Layers by Electromagnetic and Ultrasonic Diathermy," Transactions and Bimonthly Publications AIEE, 6:483(9), 483–487 (1953), explained that the variation of electromagnetic frequency permitted penetration of the fatty layer and dissipation of a large fraction of the total energy in the underlying muscle.

Aronow, in "The Use of Radio-Frequency Power in Making Lesions in the Brain," Journal of Arch. Phys. Med., Vol. 17, 431–438 (1960), describes an apparatus which used electrical energy to make lesions in the brain. In "The Technical Aspects of Electrosurgery," Oral Surgery, Oral Medicine and Oral Pathology, Vol. 36, 177–187 (1973), Friedman discussed the relationship between the nature of varying electrical waveforms and their function in cutting, coagulation and hemostasis. Curtis, in "High Frequency Currents in Endoscopy: A Review of Principles and Precautions," Gastrointestinal Endoscopy, Vol. 20, No. 1, 9–12 (1973), discussed the use of high frequency currents in endoscopic surgery.

Sozio, Riley, and Shklar, in "A Histologic and Electronic Evaluation of Electrosurgical Currents: Nonfiltered Full-wave Modulated vs. Filtered Current," Journal of Prosthetic Dentistry, Vol. 33., No. 3, 300–311 (1975), compared the healing and alternation of tissues incised by means of scalpel, non-filtered full-wave modulated current and filtered current. In "Histologic Evaluation of Electrosurgery with Varying Waveforms," Journal of Prosthetic Dentistry, Vol. 40, No. 3, 304–308 (1978), Maness, Roeber, Clark, Cataldo, Riis and Haddad described a study done to determine differences in tissue alteration produced by electrosurgical machines with different carrier frequencies and waveforms.

Krause-Hohenstein, in the article "Electrosurgery: Fundamental Requirements for Successful Use (I)," Quintessence International, Report 2252, November, 1115–1124 (1983), described the use of radio waves transmitted from the tip of an active electrode to effect incisions in oral surgery, referring to the method as radiosurgery to distinguish it from electrocautery, medical diathermy, and the use of hyfrecators. The transmitted radio waves are captured by a grounding plate which is the receiving antenna.

Literature search has failed to reveal a study or surgical procedure in which radio waves transmitted from the tip of an active electrode are employed to make surgical incisions in the cornea, sclera, uvea, anterior capsule, or lens of the human eye. Heretofore, incision of the cornea or sclera has been performed mechanically by sharp surgical blades and most recently by laser light in limited uses. Removal of the anterior capsule of the lens during extracapsular cataract surgery has been performed by sharp blade incision or by mechanically grasping a cut edge of the anterior capsule and manually pulling on the edge of the capsule to tear the capsule. Fragmentation of the nucleus of the eye lens for removal has been performed by mechanically cracking the nucleus or by mechanically chopping the lens with an oscillating microblade. These procedures have the following disadvantages:

(a) Surgical blade incision is inaccurate, results in much friction drag, and provides no substantial hemostasis.

(b) Laser incision requires extremely expensive hardware and is difficult to adapt to present day surgical applications in the operating room.

(c) Mechanical cracking of the lens nucleus is inefficient and offers poor control.

(d) Mechanically chopping the lens nucleus with an oscillating microblade is inefficient and limited by friction and other mechanically related factors, and therefore, not all lenses can be managed and treated with this modality.

(e) The oscillating microblade can permanently damage portions of the eye with which it comes in contact.

Peyman and Dodich, in "Experimental Intraocular Coagulation," Ophthalmic Surgery Vol. 3, No. 1, 32–37 (1972), described the use of what they termed a radiofrequency probe which was inserted into the eyes of test animals to coagulate the retina and intraocular blood vessels. The apparatus employed radiofrequency diathermy to generate heat in the area adjacent to the tip of the probe to cause coagulation of intraocular tissue. However, use of the apparatus entails passing electric current within the eye and creates high temperatures in the eye, and the apparatus does not provide an independent means for incising the eyeball. Use of the apparatus requires mechanical incision of the eyeball to provide a means for insertion of the device into the eye. Moreover, passing electric current within the eye may have permanently damaging effects on the cornea, retina, and optic nerve.

O'Malley, et al., U.S. Pat. No. 3,884,237, May 20, 1975 describes an apparatus which employs a high-frequency electric current electrode which moves in and out of a tubular structure, removing from the eye coagulated materials adhering to the electrode tip. However, use of this apparatus requires the passage of electric current within the eye, which may have permanently damaging effects on the cornea, retina, and optic nerve. Moreover, the apparatus creates high temperatures to coagulate eye tissue and does not supply a safe, efficient means for making surgical incisions in the eyeball globe, nor a safe and efficient means for removal of the anterior capsule of the eye lens, nor a safe and efficient means for removal of the lens nucleus.

Poler, U.S. Pat. No. 4,301,802, Nov. 24, 1981 describes an apparatus which employs electrical cauterization by means of an electrode to make circular cuts in the anterior wall of the lens capsule. However, use of the apparatus requires the passage of electric current within the eye, which may have permanently damaging effects on the cornea, retina, and optic nerve. Moreover, use of the device requires mechanical cutting into the cornea forward of the scleral ridge so that the electrocautery apparatus may be inserted into the eye. Use of the apparatus creates high temperatures in the electrode inserted into the eye and, necessarily, high temperatures in the eye tissues contacted by the electrode, which may cause permanent damage to those eye tissues contacted.

Doss, et al., U.S. Pat. No. 4,326,529, Apr. 27, 1982 describes an apparatus which employs radiofrequency electronic energy to heat the corneal stroma to effect corneal reshaping. However, use of the apparatus requires the passage of electric current within the eye, which may have permanently damaging effects on the cornea, retina, and optic nerve. Moreover, use of the apparatus creates high temperatures in eye tissue and does not provide a means for surgical incision of the eyeball.

Koziol, et al., U.S. Pat. No. 4,597,388, Jul. 1, 1986 describes a method and apparatus for cataract removal which creates an electric spark within the eye to generate an electrohydraulic shock which liquifies the lens of the eye. However, use of the apparatus requires the passage of electric current within the eye, which may have permanently damaging effects on the cornea, retina, and optic nerve. Moreover, the use of the apparatus generates an electric spark which creates high temperatures, and a shock which may cause permanent damage to portions of the eye contacted other than the lens nucleus. Also, use of the apparatus requires a mechanical incision to allow insertion of the device into the eye and the apparatus requires the use of expensive laser equipment.

Reimels, U.S. Pat. No. 5,009,656, Apr. 23, 1991 describes a method and apparatus using electrodes adapted to receive bipolar potential to create a spark to cut and coagulate body tissue. However, use of the apparatus for ocular surgery requires the passage of electric current within the eye, which may have permanently damaging effects on the cornea, retina, and optic nerve. Moreover, the creation of the spark may generate excessive heat in tissues adjacent to the electrodes, which may cause permanent damage to portions of the eye contacted by the electrodes.

SUMMARY OF THE INVENTION

My invention is a method employing low power radio waves transmitted from the tip of an active incising electrode to perform more efficient and safer ocular incisional surgery, including excision of the anterior capsule of the lens, slicing and fragmentation of the nuclei and cortex of eye cataracts, incisional surgery of the sclera and uvea of the eye, and full thickness and partial thickness incisional surgery of the cornea.

Briefly and basically, in accordance with the present invention, a method of performing surgery on an eye includes the steps of producing with a generator low power radio wave energy which is fed into an active incising electrode. A high impedance contact is provided between a surgical subject and a grounding plate connected to the generator and the incising of the ocular tissue of the surgical subject is carried out by means of low power radio wave energy transmitted from the incising tip of the active electrode. The tip of the electrode is prevented from becoming hot by use of the high impedance contact between the surgical subject and the return path via the grounding plate.

ADVANTAGES

Several advantages of the present invention are that it provides:
(a) a surgical method which produces much safer, more controlled, and more efficient eye surgery;
(b) a much improved surgical method of removing the central portion of the anterior capsule leaflet through which the nucleus and cortex of the human eye can be removed;
(c) a surgical method which produces a smooth, beaded edge opening in the anterior capsule of the eye, thereby providing an edge to this smooth capsular opening which is much stronger than is produced by the presently used capsulorhexis mechanical technique;
(d) a surgical method to repair a tear in the anterior capsular rim by excision of the torn section of the capsule;
(e) a surgical method which enables the surgeon to easily fragment and slice through even the hardest lens nuclei and cortex, thereby facilitating removal of a cataract through an extremely small incision in the eyeball globe;
(f) a surgical method which enables the surgeon to incise and fragment cataracts more efficiently than the mechanical and ultrasonic methods presently in use in eye cataract surgery;
(g) a surgical method which enables the surgeon to fragment hard lens nuclei which cannot be fragmented by presently available mechanical and ultrasonic techniques;

(h) a surgical method which provides a quicker, more efficient, and safer method of cataract removal than is available through presently employed techniques;

(i) a surgical method to produce quicker, more efficient, and safer scleral and uveal incisions, with a much reduced risk of bleeding from the incision site than is presently available through present incision techniques;

(j) a surgical method which provides a more efficient filtering surgery technique for the treatment of glaucoma, which has a much reduced risk of bleeding than traditional surgical filtering;

(k) a surgical method which produces a more efficient and safer scleral incision for access into the posterior chamber of the eye to effect posterior segment surgery and treatment of posterior segment pathology;

(l) a surgical method which produces safer, more efficient incision and sculpturing of the cornea than is available through presently used techniques, and which does not require the use of expensive laser equipment;

(m) a surgical method which produces a safer, more efficient incision of the cornea for access into the anterior chamber of the eye for surgical intervention and treatment of eye pathology;

(n) a surgical method which enables the surgeon to effect variable depth corneal incision and sculpturing of the cornea;

(o) a surgical method which enables the surgeon to incise the cornea to effect keratorefractive surgical correction of the cornea refractive power, thereby minimizing the need for post-operative eyeglasses or contact lens correction;

(p) a surgical method employing electromagnetic radiofrequency energy which produces a low amount of lateral heat in ocular tissue incised; and (q) a method of surgery employing the use of electromagnetic radiofrequency energy in which the active electrode remains cool while incising ocular tissue.

Further objects and advantages of my invention will become apparent from a consideration of the ensuing description.

DETAILED DESCRIPTION OF THE PREFERRED EMBODIMENTS

My method of ocular radiosurgery is different from all present techniques of eye surgery wherein electricity is applied for ocular use, such as electrocautery or hyfrecation. The previous techniques utilize a handpiece on which the active tip becomes hot during use. Moreover, my method of ocular radiosurgery is performed using an electromagnetic radiofrequency generator which transmits low power radio waves from the tip of the active electrode. This active electrode tip remains cool even when incising ocular tissue.

An electromagnetic wave is created in the following manner. An electromagnetic variable frequency generator is used to produce a waveform. The amplitude of this waveform is varied by processing through a signal amplifier. The signal may be processed through a full wave rectifier or a half wave rectifier. The full wave rectified signal may be further processed through a signal filter and regulator system to further smooth out the endproduct signal. The half wave rectified signal or the full wave rectified signal or the full wave rectified filtered signal is then fed into an active incising electrode for ocular surgery. A grounding plate is extended from the base of the radiosurgery equipment and is placed near the surgical subject. For highest efficiency, the surgical subject is placed between the active electrode cutting tip and the grounding plate. Since this is an electromagnetic radiofrequency system, a low impedance contact is not required between the surgical subject and the grounding plate.

The power output of the generator is a relatively low power output, less than 250 watts. Preferably, power output of the generator would be less than 100 watts. Contrary to conventional requirements of a low impedance contact to ground, the present invention utilizes a high impedance contact, preferably greater than 100,000 ohms. In practicing the present invention, typically, the ground plate is not in direct contact with the skin of the patient. Typically, the grounding plate which is connected to the electrical ground return or base of the generator is placed near the patient and for best results, the patient is placed between the incising electrode and the grounding plate.

A full wave rectified and filtered signal provides minimal blood hemostasis, a low amount of lateral heat into the ocular tissue from the radiosurgical incision, and highly efficient radiosurgical incising. A full wave rectified but nonfiltered signal provides moderate blood hemostasis, moderate amount of lateral heat into the ocular tissue from the radiosurgical incision, and moderately efficient radiosurgical incising. A half wave rectified signal produces the best blood hemostasis, a high amount of lateral heat into the ocular tissue from the radiosurgical incision, and relatively slow, inefficient radiosurgical incising.

Radiocapsulotomy. Under microscopic guidance, the low power radio waves transmitted from the tip of the active electrode are employed to incise and remove the central portion of the anterior capsule of the lens of the eye, through which the nucleus and cortex of the human lens may be removed, thereby producing a smooth edge to this capsular opening which is much stronger than is produced by the presently used capsulorhexis mechanical technique. These low power radio waves may be used to repair the anterior capsular rim, if torn, by excising the torn section of the capsule with the active tip of the electrosurgical unit, a procedure which is extremely difficult to perform with present day techniques.

Radiophacofragmentation. Under microscopic guidance, the low power radio waves transmitted from the tip of the active electrode are employed to slice, fragment, and debulk the lens nuclei and cortex, facilitating cataract removal through an extremely small incision in the eyeball globe. Use of the low power radio waves in the manner described allows fragmentation of hard nuclei that cannot be fragmented by presently available mechanical or ultrasonic techniques. Also, use of the low power radio waves in the manner described provides a safer, more efficient, and quicker method of slicing and fragmenting cataracts for removal than is available through mechanical or ultrasonic techniques.

Radiosclerotomy. The low power radio waves transmitted from the tip of the active electrode are employed to produce scleral and uveal incisions with a much reduced risk of bleeding from the incision site, providing a method for efficient filtering surgery for the treatment of glaucoma. The scleral incision provides access into the posterior chamber of the eye for posterior segment surgery and treatment of posterior segment pathology.

Radiokeratotomy. The low power radio waves transmitted from the tip of the active electrode are employed to incise and sculpture the cornea. An incision in the cornea provides access to the anterior chamber for surgical intervention and treatment of pathology. The low power radio waves are employed to effect variable depth corneal incision and sculpturing of the cornea, providing keratorefractive surgical correction of corneal refractive power which is more efficient than mechanical blade incision, safer than the use of hot tip probes which burn the cornea, and less expensive than the use of laser equipment.

Surgical filtering. The low power radio waves transmitted from the tip of the active electrode utilizing the high impedance ground path may be employed to produce improved results in various surgical procedures utilized to drain excess fluid from the anterior and the posterior chamber of the eye by surgical operations on the sclera, for example by the creation of a fistula between the anterior chamber and the subconjunctival-Tenon's tissue. The fistula bypasses the usual drainage structures and provides a route for aqueous humor to flow where it may be removed by various routes. Surgical filtering procedures per se are well known to those skilled in the art, for example see *Manual of Glaucoma Diagnosis and Management*, Krupin, published by Churchill Livingstone, 1988, pp. 204–216. Attention is also directed to Heilmann & Paton, *Atlas of Ophthalmic Surgery*, Vol. II, published by Thieme Medical Publishers, Inc., 1987, pp. 2.2–2.16 and *Glaucoma*, Vol. 9, No. 4, July/August 1987, pp. 128–130.

Accordingly, the reader will see that my method of ocular radio wave radiosurgery allows performance of more efficient and safer ocular surgery, including excision of the anterior capsule of the lens, slicing, fragmentation, and debulking of the nuclei and cortex of the lens, incisional surgery of the sclera and uvea of the eye, and full thickness or partial thickness incisional surgery of the cornea of the eye. Furthermore, my method of ocular radio wave radiosurgery has the additional advantages in that it provides:

a quicker, more efficient, and safer method of cataract removal;

a method of fragmenting hard nuclei that cannot be fragmented by presently available mechanical and ultrasonic cataract surgery techniques;

a much improved method of excising and removing the central portion of the anterior capsule of the lens which produces a mechanically stronger rim in the anterior capsular opening than is produced by any previous techniques, including capsulorhexis;

a method of incising the cornea, sclera, and uvea of the eye that does not require the mechanical use of a sharp blade or the use of expensive laser equipment;

a safer, more efficient method of incising and sculpturing the cornea during keratorefractive surgical correction of corneal refractive power which does not require the use of expensive laser equipment;

a quicker, more efficient, and safer method of producing scleral incisions, with a much reduced risk of bleeding from the incision site than can be attained mechanically by using sharp surgical blades;

a method that does not produce excessive amounts of electrical current, voltage or heat within the eye tissue; and a method that does not require placement of a heated electrode within the eye tissue.

Although the description above contains many specificities, these should not be construed as limiting the scope of the invention, but as merely providing illustrations of some of the presently preferred embodiments of this invention. Thus, the scope of the invention should be determined by the appended claims and their legal equivalents, rather than the examples given.

I claim:

1. A method of surgery on an eye, comprising the steps of:

producing with a generator low power radio wave energy;

feeding said radio wave energy into an active incising electrode, providing a high impedance contact between a surgical subject and a grounding plate connected to the generator; and incising ocular tissue of the surgical subject by means of said radio wave energy transmitted from a tip of said active incising electrode using the low power radio wave energy and the high impedance contact to prevent said active incising electrode from becoming hot.

2. The method of claim 1 wherein said step of producing said low power radio wave energy includes the step of producing a half wave rectified waveform.

3. The method of claim 1 wherein said step of producing said low power radio wave energy includes the step of producing a full wave rectified waveform.

4. The method of claim 1 wherein said step of producing said low power radio wave energy includes the step of producing a full wave rectified filtered waveform.

5. The method of claim 1 wherein said step of incising ocular tissue includes the step of incising a cornea of the eye.

6. The method of claim 5 further comprising the step of sculpturing of said cornea.

7. The method of claim 6 further comprising the step of keratorefractively surgically correcting of corneal refractive power.

8. The method of claim 5 further comprising the step of creating an entry port whereby surgical procedures within the eye may be performed.

9. The method of claim 1 wherein said step of incising ocular tissue includes the step of incising an anterior capsule of the lens of the eye.

10. The method of claim 9 further comprising the step of excising a central portion of said anterior capsule of the lens of the eye.

11. The method of claim 10 further comprising the step of excising a torn section of the capsular rim of said anterior capsule of the lens of the eye.

12. The method of claim 1 wherein said step of incising ocular tissue includes the step of incising a lens nucleus and cortex.

13. The method of claim 12 further comprising the steps of slicing, fragmenting and debulking of said lens nucleus and cortex, whereby cataract removal is facilitated.

14. The method of claim 1 wherein said step of incising ocular tissue includes the step of incising a sclera of the eye.

15. The method of claim 14 further comprising the step of surgical filtering, whereby treatment of glaucoma is facilitated by creating a drain for aqueous to the external surface of the eye.

16. The method of claim 14 further comprising the step of creating an entry port whereby surgical procedures within the eye may be performed.

17. The method of claim 1 wherein said step of incising ocular tissue includes the step of incising an uvea of the eye.

18. The method of claim 17 further comprising the step of surgical filtering, whereby treatment of glaucoma is facilitated by creating a drain for aqueous to the external surface of the eye.

19. The method of claim 1 wherein the step of providing a high impedance contact comprises placing near the surgical subject a ground plate extending from said generator.

20. The method of claim 19 further comprising placing said surgical subject between said tip of said active incising electrode and said grounding plate.

21. The method of claim 1 wherein said step of producing low power radio wave energy includes the step of selectively varying the frequency of the radio wave.

* * * * *

UNITED STATES PATENT AND TRADEMARK OFFICE
CERTIFICATE OF CORRECTION

PATENT NO.    : 5,413,574
DATED         : May 9, 1995
INVENTOR(S)   : Richard J. Fugo It is certified that error appears in the above-identified patent and that said Letters Patent is hereby corrected as shown below:

<u>Column 6,</u>
Line 18: change "100,000 ohms" to --100 ohms--

Signed and Sealed this

Fourteenth Day of August, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 5,413,574
DATED : May 9, 1995
INVENTOR(S) : Richard J. Fugo

It is certified that error appears in the above-identified patent and that said Letters Patent is hereby corrected as shown below:

This certificate supercedes certificate of correction issued August 14, 2001, the number was erroneously mentioned and should be deleted since no certificate of correction was granted.

Signed and Sealed this

Fourth Day of December, 2001

Attest:

NICHOLAS P. GODICI
Attesting Officer
Acting Director of the United States Patent and Trademark Office